United States Patent
Weiler et al.

(10) Patent No.: US 7,977,323 B2
(45) Date of Patent: Jul. 12, 2011

(54) $C_2$-$C_5$-ALKYL-IMIDAZOLE-BISPHOSPHONATES

(75) Inventors: Sven Weiler, Lorrach (DE); Leo Widler, Muenchenstein (CH); Jean Michel Rondeau, Rixheim (FR); Simona Cotesta, Basel (CH); Wolfgang Jahnke, Lorrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/323,696

(22) Filed: Nov. 26, 2008

(65) Prior Publication Data
US 2009/0143337 A1 Jun. 4, 2009

(30) Foreign Application Priority Data
Nov. 30, 2007 (EP) .................................... 07122016

(51) Int. Cl.
*A61K 31/675* (2006.01)
*C07F 9/02* (2006.01)

(52) U.S. Cl. .......................................... 514/94; 548/112
(58) Field of Classification Search .................. 548/112; 514/399, 94
See application file for complete search history.

(56) References Cited

U.S. PATENT DOCUMENTS

| 4,939,130 A | 7/1990 | Jaeggi et al. |
| 6,329,354 B1 * | 12/2001 | McOsker .................... 514/109 |

FOREIGN PATENT DOCUMENTS

| EP | 0275821 A1 | 7/1988 |
| WO | WO 95/14385 A1 | 6/1995 |
| WO | 02/43738 A | 6/2002 |
| WO | WO-02/43738 A2 * | 6/2002 |
| WO | WO 2006/039721 A2 | 4/2006 |
| WO | WO 2008/040763 A1 | 4/2008 |
| WO | WO 2008/121687 A2 | 10/2008 |
| WO | WO 2008/128056 A1 | 10/2008 |

OTHER PUBLICATIONS

Xie et al, Internet Electronic Journal of Molecular Design, 2004, vol. 3 (10), pp. 622-650.*
Kotsikorou et al, J. Med. Chem, 2003, vol. 46(14), pp. 2932-2944.*
Golub et al. Science (1999), vol. 286 531-537.*
Lala et al. Cancer and Metastasis Reviews (1998), 17(1), 91-106.*
Widler, Leo et al: "Highly Potent Geminal Bisphosphonates. From Pamidranate Disodium (Aredfa) to Zoledronic Acid (Zometa)" Journal of Medicinal Chemistry, 45( 17), 3721-3738 CODEN: JMCNAR ; ISSN: 0022-2623.
Kotsikorou, Evangelia et al: "A Quantitative Structure-Activity Relationship and Pharmacophore Modeling Investigation of Aryl-X and Heterocyclic Bisphosphonates as Bone Resorption Agents" Journal of Medicinal Chemistry , 46(14).
Xie , Aihua et al: "Quantitative structure-activity relationship study of bisphosphonates" Internet Electronic Journal of Molecular Design, 3(10), 622-650 CODEN: IEJMAT.
Cordero, Opposition to Costa Rican Patent Application N°11362 which corresponds to the PCT/EP2008/066245 "Opposition to Invention Patent Called: C2-CS-Alkyi-IMIDA20LE-Bisphosphonates", Published in the Gazette of Jun. 16, 2010 (3fd publication) Exp.11362.

* cited by examiner

*Primary Examiner* — Rebecca Anderson
*Assistant Examiner* — Samantha Shterengarts

(57) ABSTRACT

$C_2$-$C_5$-Alkyl-substituted [(imidazol-1-yl)-1-hydroxy-1-phosphono-ethyl]-phosphonic acids, as well as methods or processes for their manufacture, their use in the manufacture of pharmaceutical formulations, their use in the treatment of diseases, methods of using them in the treatment of diseases, pharmaceutical formulations encompassing them and/or the compounds for use in the treatment of diseases, are described. The compounds are able to inhibit excessive or inappropriate bone resorption and for the treatment of other diseases which are caused by excessive prenylation of target proteins, such as Hutchinson-Gilford progeria syndrome. The compounds are of the formula I,

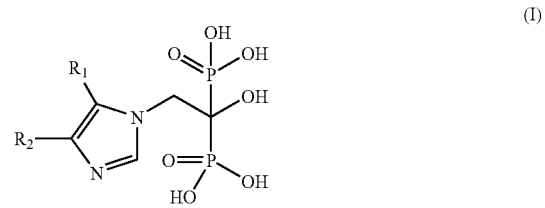

(I)

wherein one of $R_1$ and $R_2$ is hydrogen and the other is $C_2$-$C_5$-alkyl that is branched or unbranched, and can be in free form, in the form of an ester, and/or of a salt.

5 Claims, No Drawings

$C_2$-$C_5$-ALKYL-IMIDAZOLE-BISPHOSPHONATES

The present invention relates to novel $C_2$-$C_5$-alkyl-substituted [(imidazol-1-yl)-1-hydroxy-1-phosphono-ethyl]-phosphonic acids, as well as methods or processes for their manufacture, their use in the manufacture of pharmaceutical formulations, their use in the treatment of diseases, methods of using them in the treatment of diseases, pharmaceutical formulations encompassing them and/or the compounds for use in the treatment of diseases, where the diseases are especially as mentioned below. The compounds are able to inhibit excessive or inappropriate bone resorption and are also useful in the treatment of prenylation related diseases.

The invention in a first aspect, especially relates to a compound of the formula I,

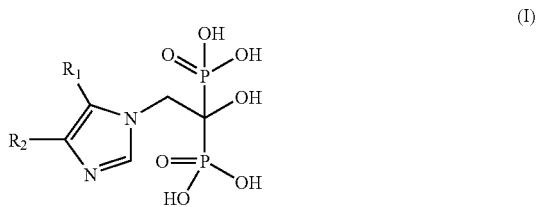

wherein one of $R_1$ and $R_2$ is hydrogen and the other is $C_2$-$C_5$-alkyl that is branched or unbranched, or an ester, and/or a salt thereof.

The general expressions used above and below preferably have the following meanings, where each more general expression, independently of others, may be replaced independently of the others or two or more or especially all may be replaced by the more specific definitions, thus defining more preferred embodiments of the invention:

Lower alkyl is for example $C_1$-$C_5$ alkyl such as methyl, ethyl, propyl or butyl, and also isobutyl, sec-butyl or tert-butyl, or pentyl, e.g. n-pentyl, isopentyl, neo-pentyl, sec.-pentyl or tert-pentyl.

Phenyl-lower alkyl is for example phenyl-$C_1$-$C_4$-alkyl, such as benzyl.

Halo(geno) (also as halogenide) is preferably fluoro, chloro, bromo or iodo.

"About" preferably means that the given numerical value may deviate by up to ±20, more preferably by up to ±10% from the given value, most preferably by ±5.

Salts of compounds of formula I are in particular the salts thereof with pharmaceutically acceptable bases (pharmaceutically acceptable salts), such as non-toxic metal salts derived from metals of groups Ia, Ib, IIa and IIb, e.g. alkali metal salts, preferably lithium or more preferably sodium or potassium salts, alkaline earth metal salts, preferably calcium or magnesium salts, copper, aluminium or zinc salts, and also ammonium salts with ammonia or organic amines or quaternary ammonium bases such as free or C-hydroxylated aliphatic amines, preferably mono-, di- or tri-lower alkylamines, e.g. methylamine, ethylamine, dimethylamine or diethylamine, mono-, di- or tri(hydroxy-lower alkyl)amines such as ethanolamine, diethanolamine or triethanolamine, tris(hydroxymethyl)aminomethane or 2-hydroxy-tert-butylamine, or N-(hydroxy-lower alkyl)-N,N-di-lower alkylamines or N-(polyhydroxy-lower alkyl)-N-lower alkylamines such as 2-(dimethylamino)ethanol or D-glucamine, or quaternary aliphatic ammonium hydroxides, e.g. with tetrabutylammonium hydroxide.

The compounds of formula I and salts thereof have valuable pharmacological properties. In particular, they inhibit the mevalonate pathway in cells and have a pronounced regulatory action on the calcium metabolism of warm-blooded animals.

Most particularly, they effect a marked inhibition of bone resorption in estrogen-deficient rats, as can be demonstrated in the experimental procedure with ovariectomized rats described by Hornby et al. Calcified Tiss Int 2003; 72:519-527 and Gasser et al J Bone Miner Res 2008; 23:544-551 after intravenous or subcutaneous administration of doses in the range from about 1 to 500 µg/kg. Tumor-associated osteolysis is likewise inhibited after intravenous or subcutaneous administration of doses in the range from about 1 to 500 µg/kg using the procedure of Peyruchaud et al. J Bone Miner Res 2001; 16:2027-2034. In addition, when similarly administered in the experimental procedure according to Newbould, Brit. J. Pharmacology 21, 127 (1963), and according to Rordorf et al. Int J Tissue React. 1987; 9(4):341-7, the compounds of formula I and salts thereof effect a marked inhibition of the progression of arthritic conditions in rodents with adjuvant and collagen arthritis, respectively.

The novel bisphosphonates are especially useful as pharmaceutical agents for human and veterinary use in the treatment of one or more diseases (this term including conditions or disorders), especially they are able to inhibit excessive or inappropriate bone resorption especially associated with diseases of bones and joints, for example benign conditions such as osteoporosis, osteopenia, osteomyelitis, osteoarthritis, rheumatoid arthritis, bone marrow edema, bone pain, reflex sympathetic dystrophy, ankylosing spondylitis (aka Morbus Bechterev), Paget's disease of bone or periodontal disease, malignant conditions such as hypercalcemia of malignancy, bone metastases associated with solid tumors and hematologic malignancies, orthopedic conditions such as prosthesis loosening, prosthesis migration, implant fixation, implant coating, fracture healing, distraction osteogenesis, spinal fusion, avascular osteonecrosis, bone grafting, bone substitutes, or any combination of two or more such conditions.

The novel bisphosphonates are also useful as pharmaceutical agents for human and veterinary use in the treatment of diseases which are caused by excessive prenylation of target proteins, such as Hutchinson-Gilford progeria syndrome. This is underlined by the fact that a bisphosphonate, in combination with a statin, has shown beneficial effects in a mouse models of human premature aging (e.g. Hutchinson-Gilford progeria syndrome) (see below).

The following publications (each of which is incorporated herein by reference, especially with regard to the description of the assays or methods mentioned below therein) describe various assays and methods that can be used to confirm the advantageous biological profile of the compounds of the formula I:

The effects of a single i.v. administration to mature, ovariectomized (OVX) rats as a model for postmenopausal osteoporosis in order to elucidate (1) the temporal changes in biochemical markers of bone turnover and femoral bone mineral density (BMD), (2) to measure changes of static and dynamic histomorphometric parameters, bone micro-architecture and mechanical strength, and (3) to assess the preventive effects of chronic treatment with a compound of the formula I on these parameters can be demonstrated as described in Calcif. Tissue Int. (2003) 72, 519-527. High activity can be found here.

The effect of a compound of the formula I on synovial inflammation, structural joint damage, and bone metabolism in rats during the effector phase of collagen-induced arthritis (CIA) can be demonstrated as shown in ARTHRITIS & RHEUMATISM (2004), 50(7), 2338-2346.

The effect of a compound of the formula I on bone ingrowth can be examined in an animal model in which porous tantalum implants are placed bilaterally within the ulnae of dogs as described in J. Bone Joint Surg. (2005), 87-B, 416-420.

Inhibition of skeletal tumor growth in a mouse model can be demonstrated in accordance with the method described in J. Natl. Cancer. Inst. (2007), 99, 322-30.

Beneficial effects of zoledronic acid in combination with pravastatin have been demonstrated in cellular experiments as well as in a mouse model of Hutchinson-Gilford progeria syndrome as described in Nat. Medicine (2008), 14, 767-772.

The x-ray structure of compounds of the formula I when bound to farnesyl pyrophosphate synthase can be obtained by or in analogy to the methods described in Chem. Med. Chem. (2006), 1, 267-273. Human FPPS, a homodimeric enzyme of 41-kDa subunits, catalyzes the two-step synthesis of the C15 metabolite farnesyl pyrophosphate (FPP) from the C5 isoprenoids dimethylallyl pyrophosphate (DMAPP) and isopentenyl pyrophosphate. FPP is required for the posttranslational prenylation of essential GTPase signaling proteins such as Ras and Rho and is also a precursor for the synthesis of cholesterol, dolichol, and ubiquinone.

For example, in a cell-free in vitro assay the superiority of compounds of the formula I over compounds already known can be shown. Briefly, the reaction proceeds in the presence of enzyme and an inhibitor of the formula I, and the reaction product (farneysyl pyrophosphate) is quantified by LC/MS/MS.

In detail, the inhibitor and enzyme are pre-incubated before adding the substrates.

The assay is a label-free assay for farnesyl pyrophosphate synthase (FPPS) based on LC/MS/MS. This method quantifies in-vitro untagged farnesyl pyrophosphate (FPP) and is suitable for high throughput screening (HTS) to find inhibitors of FPPS and for the determinations of IC50 values of candidate compounds. The analysis time is 2.0 minutes with a total cycle time of 2.5 minutes. The analysis can be formatted for 384-well plates resulting in an analysis time of 16 hours per plate.

Reagents:

Pentanol, methanol, and isopropyl alcohol are HPLC grade and obtained from Fisher Scientific. DMIPA is from Sigma-Aldrich. Water is from an in-house Milli-Q system. The assay buffer (20 mM HEPES, 5 mM $MgCl_2$ and 1 mM $CaCl_2$) is prepared by dilution from 1 mM stock solutions obtained from Sigma-Aldrich. Standards of geranyl pyrophosphate (GPP), isoprenyl pyrophosphate (FPP), and farnesyl S-thiolopyrophosphate (FSPP) are from Echelon Biosciences (Salt Lake City, Utah). Human farnesyl pyrophosphate synthase (FPPS, Swissprot ID: P14324) (13.8 mg/mL) is prepared as described by Rondeau et al (ChemMedChem 2006, 1, 267-273).

Assay:

LC/MS/MS analyses are performed on a Micromass Quattro Micro tandem quadrupole mass analyser (Waters Corp., Milford, Mass., USA) interfaced to an Agilent 1100 binary LC pump Agilent Technologies, Inc., Santa Clara, Calif., USA). Injection is performed with a CTC Analytics autosampler (Leap Technologies Inc., Carrboro, N.C., USA) using an injection loop size of 2.5 μL. Chromatography is performed on a Waters 2.1×20 mm Xterra MS C18 5 μm guard column (P/N186000652) (Waters Corp., Milford, Mass., USA) contained in a guard column holder (P/N 186000262) using 0.1% DMIPA/methanol as solvent A and 0.1% DMIPA/water as solvent B (DMIPA is dimethylisopropylamine). The gradient is 5% A from 0.00 to 0.30 min., 50% A at 0.31 min., 80% A at 1.00 min., and 5% A from 1.01 to 2.00 min. The flow rate is 0.3 mL/min, and the flow is diverted to waste from 0.00 to 0.50 min and again from 1.20 to 2.00 min.

The Multiple Reaction Monitoring (MRM) transitions monitored are 381->79- for FPP and 397->159- for FSPP at a collision energy of 22 eV and a collision cell pressure of 2.1×10-3 mbar of Ar. The dwell time per transition is 400 msec with a span of 0.4 Da. The inter-channel delay and interscan delay are both 0.02 sec. Other mass spectrometric operating parameters are: capillary, 2.0 kV; cone, 35 V; extractor, 2.0 V; source temp., 100° C.; desolvation gas temp., 250° C.; desolvation gas flow, 650 L/hr; cone gas flow, 25 L/hr; multiplier, 650 V.

The total cycle time per sample is 2.5 minutes. Since the analysis is formatted for 384-well plates, a plate is analyzed in 16 hours. The chromatograms are processed using Quanlynx software, which divides the area of individual FPP peaks by the area of the FSPP peaks (internal standard). The resulting values are reported as the relative response for the corresponding sample well.

FPPS Assay Procedure

Into each well of a 384-well plate, 5 μL of compound in 20% DMSO/water is placed. 10 μL of FPPS (diluted 1 to 80000 with assay buffer) is added to each well and allowed to pre-incubate with the compound for 5 minutes. At that time, 25 μL of GPP/IPP (5 μM each in assay buffer) is then added to start the reaction. After 30 minutes the reaction is stopped by addition of 10 μL of 2 μM FSPP in 2% DMIPA/IPA. The reaction mixture is then extracted with 50 μL of n-pentanol using vortex mixing. After phase separation, 25 μL of the upper (n-pentanol) layer is transferred to a new 384-well plate and the pentanol is evaporated using a vacuum centrifuge. The dried residue is reconstituted in 50 μL of 0.1% DMIPA/water for analysis by the LC/MS/MS method.

FSPP is used as the internal standard for the mass spectra. A phosphate moiety generates an (M–H)– ion as the base peak in the spectra.

The compounds of the invention preferably, in this test system, have an $IC_{50}$ in the range from 0.8 to 10 nM, the preferred ones preferably from 0.9 to 3.3 nM. Especially, they show a surprising superiority over compounds in the prior art, e.g. [2-(5-ethyl-imidazol-1-yl)-1-hydroxy-1-phosphono-ethyl]-phosphonic acid.

The utility of the assay for $IC_{50}$ determinations is validated using zoledronic acid, a known bisphosphonate inhibitor of FPPS.

The invention in particular relates to a compound of the formula I wherein $R_1$ is $C_2$-$C_5$-alkyl, especially propyl, isopropyl, n-butyl, sec-butyl, tert-butyl, isobutyl or especially ethyl, and $R_2$ is hydrogen, or an ester thereof, and/or an (especially pharmaceutically acceptable) salt thereof.

The invention in particular alternatively relates to a compound of the formula I wherein $R_1$ is hydrogen and $R_2$ is $C_2$-$C_5$-alkyl, especially propyl, isopropyl, n-butyl, sec-butyl, tert-butyl, isobutyl or especially ethyl, or an ester thereof, and/or an (especially pharmaceutically acceptable) salt thereof.

Preferred is a compound of the formula I wherein $R_1$ is hydrogen and $R_2$ is ethyl, or an ester thereof, and/or an (especially pharmaceutically acceptable) salt thereof.

Most preferred is a compound of the formula I wherein $R_1$ is ethyl and $R_2$ is hydrogen, or an ester thereof, and/or an (especially pharmaceutically acceptable) salt thereof.

A compound according to the invention can be prepared according to methods that, for different compounds, are known in the art. For example, based at least on the novel products obtained and/or the novel educts employed, a novel process is preferred comprising reacting a carboxylic acid compound of the formula II,

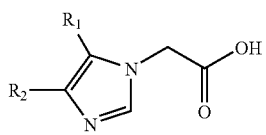

(II)

wherein $R_1$ and $R_2$ are as defined for a compound of the formula I, with phosphorous oxyhalogenide to give a compound of the formula I, or a salt thereof, and, if desired, converting an obtainable free compound of the formula I into its salt, converting an obtainable salt of a compound of the formula I into the free compound and/or converting an obtainable salt of a compound of the formula I into a different salt thereof.

As phosphorous oxyhalogenide, phosphorous oxychloride ($POCl_3$) is especially preferred. The reaction preferably takes place in a customary solvent or solvent mixture, e.g. in an aromatic hydrocarbon, such as toluene, at preferably elevated temperatures, e.g. in the range from 50° C. to the reflux temperature of the reaction mixture, e.g. from (about) 80 to (about) 120° C.

Free compounds of formula I can be converted into basic salts by partial or complete neutralisation with one of the bases mentioned at the outset.

Salts can be converted in a manner known per se into the free compounds, for example by treatment with an acid reagent such as a mineral acid.

The compounds, including their salts, can also be obtained in the form of hydrates or may contain the solvent used for crystallisation in their crystal structure.

Because of the close relationship between the novel compounds in the free form and in the form of their salts, the references made throughout this specification to the free compounds and their salts also apply by analogy to the corresponding salts and free compounds.

The invention also relates to those embodiments of the process in which a compound obtainable as intermediate at any stage of the process is used as starting material and the remaining steps are carried out, or a starting material is used in the form of a salt or, preferably, is formed under the reaction conditions.

The starting materials can, for example preferably, be obtained by saponifying a compound of the formula III,

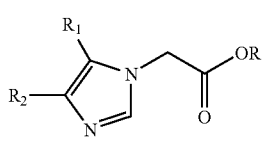

(III)

wherein $R_1$ and $R_2$ are as defined for a compound of the formula I and R is unsubstituted or substituted alkyl, especially lower alkyl or phenyl-lower alkyl, in the presence of an appropriate acid, e.g. a hydrohalic acid, such as hydrochloric acid, preferably in the presence of an aqueous solvent, such as water, at preferably elevated temperatures, e.g. in the range from (about) 50 to (about) 100° C., e.g. from 80 to 100° C., to give the compound of the formula II, or a salt thereof.

A compound of the formula III can, for example preferably, be obtained by reacting an imidazole compound of the formula IV,

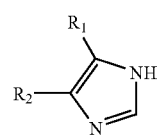

(IV)

wherein $R_1$ and $R_2$ are as defined for a compound of the formula I, with an ester of the formula V,

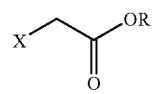

(V)

wherein R is as defined for a compound of the formula III and X is halogen, especially fluoro, chloro, iodo or especially bromo, lower-alkanesulfonyloxy or toluenesulfonyloxy, preferably in the presence of a strong base, such as an alkaline metal alcoholate, especially potassium tert-butylate, in an appropriate solvent or solvent mixture, e.g. a cyclic ether, such as tetrahydrofurane, preferably at temperatures in the range from (about) −10 to (about) 80° C., e.g. from 20 to 30° C. Where required, resulting mixtures of compounds of the formula III (wherein in one compound $R_1$ is $C_2$-$C_5$-alkyl and $R_2$ is hydrogen, in the other $R_2$ is $C_2$-$C_5$-alkyl and $R_1$ is hydrogen) can be separated e.g. by chromatographic methods, differential crystallisation or the like.

Starting materials of the formulae IV and V, as well as any other starting materials employed not described so far, can be obtained by methods that are known in the art or in analogy thereto, are commercially available and/or can be made in analogy to methods described herein.

The invention also relates to any novel process step or combination of process steps, as well as to any novel starting material(s) or intermediate(s), or (a) salt(s) thereof.

Esters of a compound of the formula I can, for example, be prepared in analogy to methods described in the prior art for comparable compounds.

The pharmaceutical compositions which contain the compounds of formula I, or pharmaceutically acceptable non-toxic salts thereof, are those for enteral such as oral, or rectal and parenteral, administration to warm-blooded animals, the pharmacological active ingredient being present alone or together with a pharmaceutically suitable carrier.

The novel pharmaceutical compositions comprise e.g. from about 0.0001 to 80%, preferably from about 0.001 to 10%, of the active ingredient. Pharmaceutical compositions for enteral or parenteral administration are e.g. those in dosage unit forms such as dragees, tablets, capsules or suppositories, as well as ampoules, vials, pre-filled syringes. These pharmaceutical compositions are prepared in a manner known per se, for example by conventional mixing, granulating, confectioning, dissolving or lyophilising methods. For example, pharmaceutical compositions for oral administration can be obtained by combining the active ingredient with solid carriers, optionally granulating a resulting mixture and processing the mixture or granulate, if desired or necessary after the addition of suitable excipients, to tablets or dragee cores.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or polyvinylpyrrolidone, and/or, if desired, disintegrators, such as the abovementioned starches, also carboxymethyl starch, crosslinked polyvinylpyrrolidone, agar, alginic acid or a salt thereof such as sodium alginate. Excipients are in particular glidants and lubricants, for example silica, talcum, stearic acid or salts thereof such as magnesium stearate or calcium stearate, and/or polyethylene glycol. Dragee cores are provided with suitable coatings which can be resistant to gastric juices, using inter alia concentrated sugar solutions which may contain gum arabic, talcum, polyvinylpyrrolidone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropyl methyl cellulose phthalate. Dyes or pigments can be added to the tablets or dragee coatings, for example to identify or indicate different doses of active ingredient.

Further pharmaceutical compositions for oral administration are dry-filled capsules made of gelatin or hypromellose and also soft sealed capsules consisting of gelatin and a plasticiser such as glycerol or sorbitol. The dry-filled capsules can contain the active ingredient in the form of granules, for example in admixture with fillers such as lactose, binders such as starches, and/or glidants such as talcum or magnesium stearate, and optionally stabilisers. In soft capsules, the active ingredient is preferably dissolved or suspended in a suitable liquid, such as a fatty oil, paraffin oil or a liquid polyethylene glycol, to which a stabiliser can also be added.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols. It is also possible to use gelatin rectal capsules which contain a combination of the active ingredient with a base material. Suitable base materials are e.g. liquid triglycerides, polyethylene glycols and paraffin hydrocarbons.

Particularly suitable dosage forms for parenteral administration (which is especially preferred) are aqueous solutions of an active ingredient in water-soluble form, for example a water-soluble salt. The solution may be adjusted with inorganic or organic acids or bases to a physiologically acceptable pH value of about pH 4-9 or most preferably of about 5.5-7.5. The solutions further may be made isotonic with inorganic salts like sodium chloride, or organic compounds like sugars, sugar alcohols, or amino acids, most preferably with mannitol or glycerol. Suitable compositions are also suspensions of the active ingredient, such as corresponding oily injection suspensions, for which there are used suitable lipophilic solvents or vehicles such as fatty oils, for example sesame oil, or synthetic fatty acid esters, for example ethyl oleate or triglycerides, or aqueous injection suspensions which contain substances which increase the viscosity, for example sodium carboxymethyl cellulose, sorbitol and/or dextran, and optionally also stabilisers.

The present invention also relates to the use of the compounds of formula I and salts thereof preferably for the treatment of inflammatory conditions, primarily to diseases associated with impairment of calcium metabolism, e.g. rheumatic diseases and, in particular, osteoporosis.

Parenteral Doses below 0.1 µg/kg of body weight affect hard tissue metabolism only insignificantly. Long-term toxic side-effects may occur at doses of over 1000 µg/kg of body weight. The compounds of formula I and salts thereof can be administered orally, as well as subcutaneously, intramuscularly or intravenously in iso- or hypertonic solution. Preferred daily doses are, for oral administration, in the range from about 1 to 100 mg/kg, for intravenous, subcutaneous and intramuscular administration in the range from about 20 to 500 µg/kg.

The dosage of the compounds of formula I and salts thereof is, however, variable and depends on the respective conditions such as the nature and severity of the illness, the duration of treatment and on the respective compound. Dosage unit form for parenteral, e.g. intravenous, administration contain e.g. from 10 to 300 µg/kg of body weight, preferably from 15 to 150 µg/kg body weight; and oral dosage unit forms contain e.g. from 0.1 to 5 mg, preferably from 0.15 to 3 mg per kg body weight. The preferred single dose for oral administration is from 10 to 200 mg and, for intravenous administration, from 1 to 10 mg. The higher doses for oral administration are necessary on account of the limited absorption. In prolonged treatment, the dosage can normally be reduced to a lower level after an initially higher dosage in order to maintain the desired effect. Parenteral, (e.g. intravenous or subcutaneous) doses may be administered intermittently at regular intervals between 1 and 52 times per year. Oral doses may be administered regularly on a daily, weekly, monthly or quarterly dosing regimen.

The invention also relates to a method of treatment of an animal, especially a human, comprising administering to an animal, especially a human, in need thereof an amount of a compound of the formula I, an ester and/or a pharmaceutically acceptable salt thereof sufficient (effective) for the treatment of a disease as mentioned above.

The invention also relates to a pharmaceutical formulation, especially an infusion or injection solution, comprising a compound of the formula I, an ester and/or a salt thereof, and at least one pharmaceutically acceptable carrier material.

The following non-limiting examples illustrate the invention without limiting its scope.

If not mentioned otherwise, temperatures are given in degree Celsius (° C.). Where no temperature is mentioned, the reaction or other method step takes place at room temperature.

Abbreviations:
Ac. acetyl
aq. Aqueous
DMSO dimethyl sulfoxide
Et ethyl
h hour(s)
HPLC high performance liquid chromatography
KOtBu potassium tert-butylate
Me methyl
ml milliliter(s)
NMR Nuclear Magnetic Resonance
rt room temperature
THF tetrahydrofurane
4-Ethylimidazole and all other imidazole derivatives are prepared according to D. Horne et al., Heterocycles, 1994, Vol. 39, No. 1, p. 139-153.

EXAMPLE 1

[2-(4-Ethyl-imidazol-1-yl)-1-hydroxy-1-phosphono-ethyl]-phosphonic acid 650 mg (3.38 mmol) (4-ethyl-imidazol-1-yl)-acetic acid are dissolved in 15 ml toluene at rt under nitrogen. 852 mg (3 mmol) $H_3PO_3$ are added and the mixture is heated to 80° C. 0.936 ml (3 mmol) $POCl_3$ are added drop wise. The resulting mixture is heated to 120° C. and stirred overnight. The solvent is decanted off, 15 ml 6N HCl is added and the mixture is heated for three hours at reflux.

The resulting pale yellow solution is concentrated in vacuo. After dilution with acetone (25 ml) the mixture is stirred vigorously with acetone (5×25 ml) until a grey solid is formed. The grey solid is dried in high vacuo and crystallized from EtOH/water to give the title compound.

HPLC-MS: t=0.31 min, (M–H)–=299; $^1$H-NMR ($D_2O$/NaOD): δ=1.07 (t, 3H), 2.53 (q, 2H), 4.45 (t, 2H), 7.08 (s, 1H), 8.40 (s, 1H), $^{31}$P-NMR ($D_2O$/NaOD): δ=15.04 ppm Synthesis Overview:

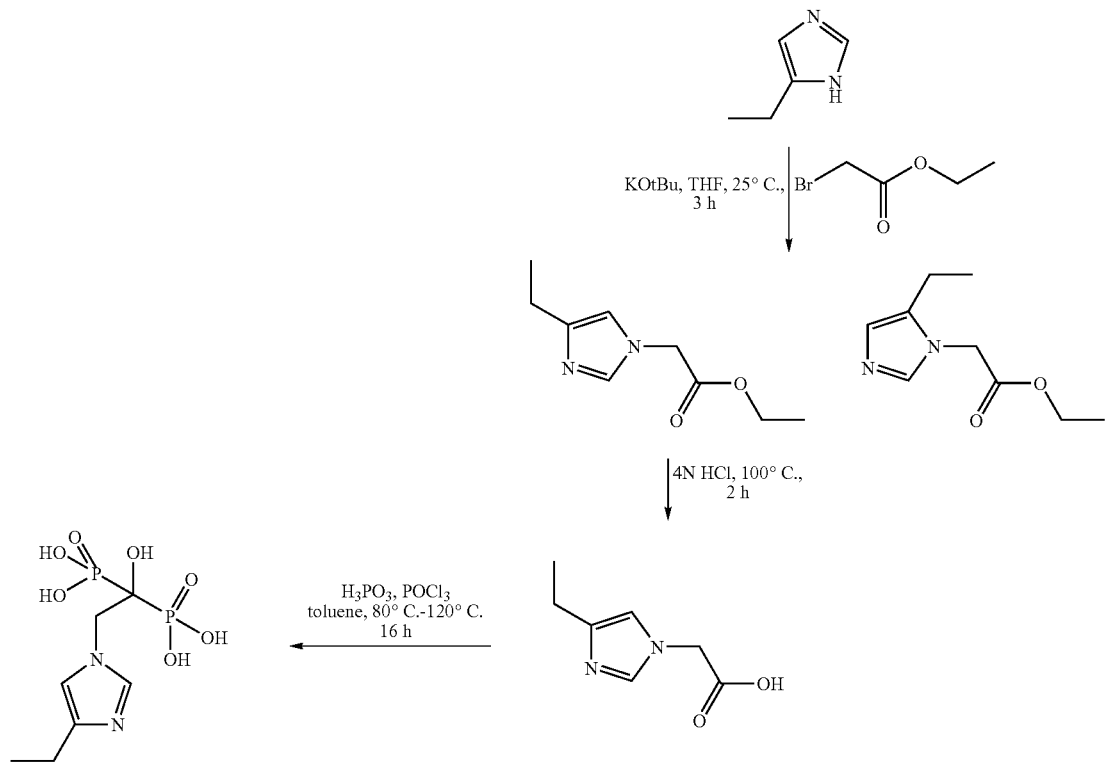

HPLC-MS Conditions:
Column: XTerra (Waters Corp., Milford, Mass., USA) 3×30 mm, 2.5 μm, C18
Solvent A: water, 5% acetonitrile, 1% HCOOH
Solvent B: acetonitrile, 1% HCOOH

|  | min | % B |
|---|---|---|
| Gradient: | 0.0 | 01 |
|  | 0.5 | 01 |
|  | 2.5 | 30 |
|  | 3.5 | 95 |
|  | 4.5 | 95 |
|  | 4.9 | 01 |

The starting materials are prepared as follows:

Step 1: (4-Ethyl-imidazol-1-yl)-acetic acid ethyl ester and (5-ethyl-imidazol-1-yl)-acetic acid ethyl ester 5.02 g (50 mmol) of 4-ethylimidazole are dissolved in 100 ml THF at rt under nitrogen. 5.9 g (52 mmol) KOtBu is added and the reaction is stirred for 2 h at rt. 6.3 ml (55 mmol) ethyl bromoacetate is added drop wise over a period of 30 min and the resulting mixture is stirred at rt for 2.5 h. 20 ml $H_2O$ and 130 ml AcOEt are added, the organic layer is separated and the aq. layer is washed again 2× with 100 ml AcOEt. The combined organic layer is washed with brine, dried over $MgSO_4$ and concentrated in vacuo. The reaction is purified by Flash-chromatography (silica gel, MeOH/methylen chloride) to give (4-ethyl-imidazol-1-yl)-acetic acid ethyl ester and (5-ethyl-imidazol-1-yl)-acetic acid ethyl ester, respectively.

(4-Ethyl-imidazol-1-yl)-acetic acid ethyl ester: HPLC-MS: t=0.60 min; 100 area %, MH+=183; $^1$H-NMR ($d_6$-DMSO) δ=1.09 (t, 3H), 1.18 (t, 3H), 2.43 (q, 2H), 4.13 (q, 2H), 4.83 (s, 2H), 6.78 (s, 1H), 7.43 (s, 1H)

(5-Ethyl-imidazol-1-yl)-acetic acid ethyl ester: HPLC-MS: t=0.72 min, 100 area %, MH+=183; $^1$H-NMR ($d_6$-DMSO): δ=1.12 (t, 3H), 1.18 (t, 3H), 2.40 (q, 2H), 4.14 (q, 2H), 4.85 (s, 2H), 6.61 (s, 1H), 7.48 (s, 1H)

Step 2: (4-Ethyl-imidazol-1-yl)-acetic acid 1.7 g (9.5 mmol) of (4-ethyl-imidazol-1-yl)-acetic acid ethyl ester are dissolved in 47 ml (190 mmol) 4N HCl and the mixture is heated to reflux. After 2 h the mixture is cooled to rt and the solvent is removed in vacuo. The resulting product is used without further purification.

MS: MH+=155, $^{1}$H-NMR (DMSO): δ=1.18 (t, 3H), 2.65 (q, 2H), 5.07 (s, 2H), 7.43 (d, 1H), 9.0 (d, 1H)

EXAMPLE 2

[2-(5-Ethyl-imidazol-1-yl)-1-hydroxy-1-phosphono-ethyl]-phosphonic acid

[2-(5-Ethyl-imidazol-1-yl)-1-hydroxy-1-phosphono-ethyl]-phosphonic acid is synthesized according to the synthesis outlined above from the corresponding (5-ethyl-imidazol-1-yl)-acetic acid ethyl ester which is the second product of step 1 in Example 1.

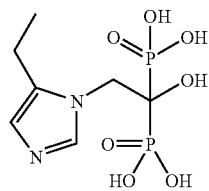

HPLC-MS: t=0.32 min, (M–H)–=299; $^{1}$H-NMR (D$_2$O/NaOD): δ=1.10 (t, 3H), 2.63 (q, 2H), 4.43 (t, 2H), 6.95 (s, 1H), 8.54 (s, 1H), $^{31}$P-NMR(D$_2$O/NaOD): δ=14.96 ppm In analogy to the above described procedures the following compounds are prepared:

EXAMPLE 3

[2-(4-Propyl-imidazol-1-yl)-1-hydroxy-1-phosphono-ethyl]-phosphonic acid

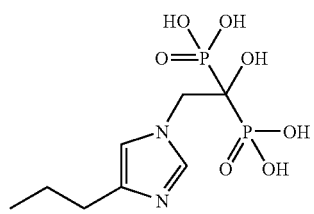

HPLC-MS: t=0.44 min, (M–H)–=313.1; $^{1}$H-NMR (D$_2$O/NaOD): δ=0.78 (t, 3H), 1.52 (m, 2H), 2.52 (t, 2H), 4.50 (t, 2H) 7.13 (s, 1H), 8.45 (s, 1H); $^{31}$P-NMR (D$_2$O/NaOD) δ=15.25 ppm

EXAMPLE 4

[2-(5-Propyl-imidazol-1-yl)-1-hydroxy-1-phosphono-ethyl]-phosphonic acid

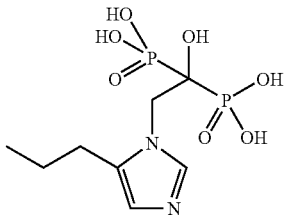

HPLC-MS: t=0.46 min, (M–H)–=313.1; $^{1}$H-NMR (D$_2$O/NaOD): δ=0.81 (t, 3H), 1.51 (m, 2H), 2.60 (t, 2H), 4.44 (t, 2H), 6.96 (s, 1H), 8.54 (s, 1H); $^{31}$P-NMR (D$_2$O/NaOD) δ=15.06 ppm

EXAMPLE 5

[2-(4-Butyl-imidazol-1-yl)-1-hydroxy-1-phosphono-ethyl]-phosphonic acid

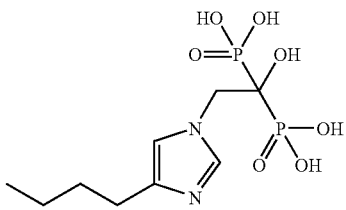

HPLC-MS: t=0.56 min, (M–H)–=327.2; $^{1}$H-NMR (D$_2$O/NaOD): δ 0.73 (t, 3H), 1.17 (m, 2H), 1.46 ( m, 2H), 2.51 (t, 2H), 4.44 (t, 2H ) 7.09 (s, 1H), 8.40 (s, 1H); $^{31}$P-NMR (D$_2$O/NaOD): δ=14.98 ppm

EXAMPLE 6

[2-(5-Butyl-imidazol-1-yl)-1-hydroxy-1-phosphono-ethyl]-phosphonic acid

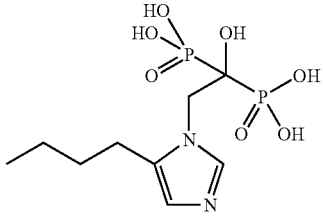

HPLC-MS: t=0.44 min, (M–H)–=327.2; $^1$H-NMR (D$_2$O/NaOD): δ=0.79 (t, 3H), 1.27 (m, 2H), 1.51 (m, 2H), 2.67 (t, 2H), 4.49 (t, 2H), 6.99 (s, 1H), 8.58 (s, 1H); $^{31}$P-NMR (D$_2$O/NaOD): δ=15.16 ppm

EXAMPLE 7

[1-Hydroxy-2-(4-isopropyl-imidazol-1-yl)-1-phosphono-ethyl]-phosphonic acid

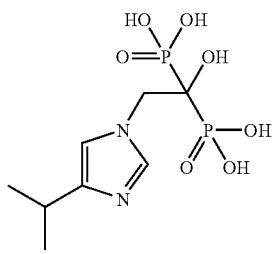

HPLC-MS: t=0.42 min, (M–H)–=313; $^1$H-NMR (d$_6$-DMSO): δ=1.13, 1.15 (d, 6H), 2.86-2.95 (m, 1H), 4.49 (t, 2H), 7.12 (s, 1H), 8.46 (s, 1H); $^{31}$P-NMR (d$_6$-DMSO): δ=15.35 ppm

EXAMPLE 8

[[1-Hydroxy-2-(5-isopropyl-imidazo-1-yl)-1-phosphono-ethyl]-phosphonic acid

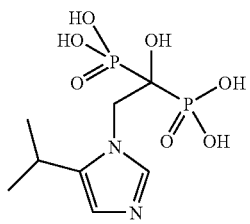

HPLC-MS: t=0.40 min, (M–H)–=313; $^1$H-NMR (d$_6$-DMSO): δ=1.10, 1.12 (d, 6H), 3.12-3.19 (m, 1H), 4.52 (t, 2H), 7.01 (s, 1H), 8.56 (s, 1H); $^{31}$P-NMR (d$_6$-DMSO): δ=15.24 ppm

EXAMPLE 9

[{2-[4-(1-Ethyl-propyl)-imidazol-1-yl]-1-hydroxy-1-phosphono-ethyl}-phosphonic acid

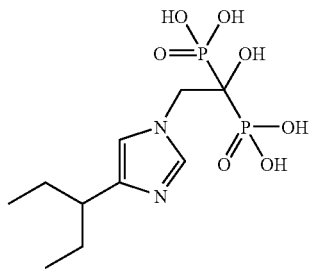

EXAMPLE 10

{2-[5-(1-Ethyl-propyl)-imidazol-1-yl]-1-hydroxy-1-phosphono-ethyl}-phosphonic acid

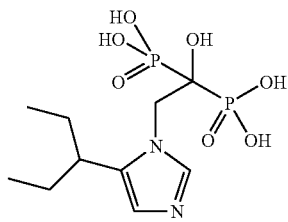

EXAMPLE 11

Injection or Infusion Solution

A 0.2% injection or infusion solution can be prepared e.g. as follows:

Active ingredient, e.g. the compound of Example 1 or 2, or a salt thereof, sodium hydroxide, sodium chloride, and water for injection are mixed to make up 2500.0 ml.

22.0 g of sodium chloride is dissolved in approx. 2000 mL of water for injections. The active ingredient is added and the pH is adjusted to e.g. pH 6.5. Water for injections is added to make up 2500 ml. The solution is filtered through a sterilizing grade filter (e.g. with a 0.2 μm pore size) To prepare unit dosage forms, 1.0 or 2.5 ml of the solution are filled into sterilized and depyrogenized glass ampoules or vials (each containing 2.0 or 5.0 mg of active ingredient). Vials are closed with sterilized and depyrogenized rubber stoppers. The stoppers are secured with an aluminum crimp cap.

In like manner, a solution of another compound of formula I obtained in Examples 3-10 can also be prepared which compound may also be in the form of a salt with a base, e.g. as sodium salt. In the latter case the solution is adjusted to the desired pH value with an acid, e.g. diluted hydrochloric acid.

The invention claimed is:

1. A compound of the formula I,

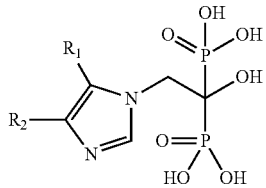

wherein one of $R_1$ and $R_2$ is hydrogen and the other is ethyl, or an ester, and/or a salt thereof.

2. A compound of the formula I according to claim 1 wherein
$R_1$ is hydrogen and
$R_2$ is ethyl,
or an ester thereof, and/or a salt thereof.

3. A compound of the formula I according to claim 1, wherein
$R_1$ is ethyl and
$R_2$ is hydrogen,
or an ester thereof, and/or a salt thereof.

4. A pharmaceutical composition, comprising a compound of the formula I, an ester and/or a pharmaceutically acceptable salt thereof, according to claim 1 and at least one pharmaceutically acceptable carrier.

5. A method of treatment of osteopenia, osteomyelitis, osteoarthritis, rheumatoid arthritis, bone marrow edema, bone pain, reflex sympathetic dystrophy, ankylosing spondylitis, Paget's disease, or hypercalcemia of malignancy in an animal, the method, comprising the step of administering to the animal an amount of a compound of the formula I, an ester and/or a pharmaceutically acceptable salt thereof, according to claim 1.

* * * * *